US005436008A

United States Patent [19]

Richter et al.

[11] Patent Number: 5,436,008
[45] Date of Patent: Jul. 25, 1995

[54] SANITIZING COMPOSITIONS

[75] Inventors: Francis L. Richter, Circle Pines; Duane J. Reinhardt, Maplewood, both of Minn.

[73] Assignee: Ecolab Inc., St. Paul, Minn.

[21] Appl. No.: 102,643

[22] Filed: Aug. 5, 1993

Related U.S. Application Data

[63] Continuation-in-part of Ser. No. 989,507, Dec. 11, 1992, Pat. No. 5,234,719.

[51] Int. Cl.$^6$ ............................................. A01N 25/08
[52] U.S. Cl. ................................... 424/405; 514/557; 424/409
[58] Field of Search .................... 424/405; 514/557

[56] References Cited

U.S. PATENT DOCUMENTS

| 349,852 | 9/1986 | Marchand | 426/332 |
|---|---|---|---|
| 1,772,975 | 8/1930 | Wieland | 514/557 |
| 2,466,663 | 4/1949 | Russ et al. | 514/494 |
| 3,297,456 | 1/1967 | Newell | 106/3 |
| 3,650,965 | 3/1972 | Cantor et al. | 252/106 |
| 3,867,300 | 2/1975 | Karabinos et al. | 252/106 |
| 3,915,633 | 10/1975 | Ramachandrau | 8/137 |
| 4,002,775 | 1/1977 | Kabara | 426/532 |
| 4,011,346 | 3/1977 | Ernst | 426/104 |
| 4,051,058 | 9/1977 | Bowing et al. | 252/186 |
| 4,051,059 | 9/1977 | Bowing et al. | 252/186 |
| 4,203,765 | 5/1980 | Claeys et al. | 430/252 |
| 4,376,787 | 3/1983 | Lentsch et al. | 424/315 |
| 4,404,040 | 9/1983 | Wang | 134/22.14 |
| 4,406,884 | 9/1983 | Fawzi et al. | 424/81 |
| 4,410,442 | 10/1983 | Lucas et al. | 252/107 |
| 4,430,381 | 2/1984 | Harvey et al. | 428/284 |
| 4,534,945 | 8/1985 | Hopkins et al. | 423/273 |
| 4,557,935 | 12/1985 | af Ekenstam et al. | 424/130 |
| 4,647,458 | 3/1987 | Ueno et al. | 424/128 |
| 4,715,980 | 12/1987 | Lopes et al. | 252/106 |
| 4,776,974 | 10/1988 | Stanton et al. | 252/106 |
| 4,900,721 | 2/1990 | Bansemir et al. | 514/25 |
| 4,920,100 | 4/1990 | Lehmann et al. | 514/23 |
| 4,945,110 | 7/1990 | Brokken et al. | 514/517 |
| 4,975,217 | 12/1990 | Brown-Skrobot et al. | 252/107 |
| 5,013,560 | 5/1991 | Stentz et al. | 424/653 |
| 5,017,617 | 5/1991 | Kihara et al. | 514/635 |
| 5,200,189 | 4/1993 | Oakes et al. | 424/405 |
| 5,208,257 | 5/1993 | Kabara | 514/552 |
| 5,246,716 | 9/1993 | Sedun et al. | 424/713 |

FOREIGN PATENT DOCUMENTS

| 1139610 | 11/1962 | Australia . |
| 1174976 | 9/1984 | Canada . |
| 0021504 | 1/1981 | European Pat. Off. . |
| 0068552 | 1/1983 | European Pat. Off. . |
| 0083820 | 7/1983 | European Pat. Off. . |
| 0097995 | 1/1984 | European Pat. Off. . |
| 0147102 | 7/1985 | European Pat. Off. . |
| 0218441 | 4/1987 | European Pat. Off. . |
| 0244144 | 11/1987 | European Pat. Off. . |
| 0245928 | 11/1987 | European Pat. Off. . |
| 0252276 | 1/1988 | European Pat. Off. . |
| 0288689 | 11/1988 | European Pat. Off. . |
| 0375827 | 7/1990 | European Pat. Off. . |
| 2122284 | 9/1972 | France . |
| 2223049 | 10/1974 | France . |
| 1937682 | 1/1970 | Germany . |

(List continued on next page.)

OTHER PUBLICATIONS

Stewart et al., *Food Science and Technology*, "A Series of Monographs", pp. 186–187.

(List continued on next page.)

*Primary Examiner*—Thurman K. Page
*Assistant Examiner*—Neil Levy
*Attorney, Agent, or Firm*—Merchant, Gould, Smith, Edell, Welter & Schmidt

[57] ABSTRACT

This invention is a microbicidal and tuberculocidal composition comprising a major portion of carrier and an effective sanitizing amount of octanoic acid, or octanoic acid derivatives, and a sulfur containing compound. Optionally, the invention may also comprise any variety of formulatory ingredient options or application adjuvants. The invention comprises concentrate compositions and methods of sanitizing and disinfecting using the antimicrobial composition of the invention.

9 Claims, No Drawings

FOREIGN PATENT DOCUMENTS

| | | |
|---|---|---|
| 59-157007 | 9/1984 | Japan . |
| 59-164400 | 9/1984 | Japan . |
| 62-048612 | 3/1987 | Japan . |
| 62-270509 | 11/1987 | Japan . |
| 1135643 | 12/1968 | United Kingdom . |
| 2076286 | 12/1981 | United Kingdom . |
| 2103089 | 2/1983 | United Kingdom . |
| 2187097 | 9/1987 | United Kingdom . |
| 2189394 | 10/1987 | United Kingdom . |
| 2211093 | 6/1989 | United Kingdom . |
| 1595431 | 5/1991 | U.S.S.R. . |
| 83/00163 | 1/1983 | WIPO . |
| 87/03799 | 7/1987 | WIPO . |
| 87/06470 | 11/1987 | WIPO . |
| 91/05842 | 5/1991 | WIPO . |

OTHER PUBLICATIONS

Towle et al., *Industrial Gums Polysaccharides and Their Derivatives*, Second Edition, Chapter XIX, Pectin, pp. 429–455.

Gosselin et al., *Clinical Toxicology of Commercial Products*, Fifth Edition, Section III, Ethylene Glycol, p. 172 (1984).

Mulder et al., *Spelderholt Centre for Poultry Research and Extension*, "Salmonella Decontamination of Broiler Carcasses with Lactic Acid, L-Cysteine, and Hydrogen Peroxide", vol. 66, pp. 1555–1557.

Kirk–Othrem, *Encyclopedia of Chemical Technology*, Third Edition, vol. 12, "Gravity Concentration to Hydrogen Energy", pp. 46–62.

Kirk–Othmer, *Encyclopedia of Chemical Technology*, Third Edition, vol. 7, "Dicarboxylic Acids", pp. 614–628.

Kirk–Othmer, *Encyclopedia of Chemical Technology*, Third Edition, vol. 4, "Carbonated Beverages", pp. 712–713.

Kirk–Othmer, *Encyclopedia of Chemical Technology*, Third Edition, vol. 6, "Citric Acid", pp. 150–179.

Kirk–Othmer, *Encyclopedia of Chemical Technology*, Third Edition, vol. 13, "Hydroxy Carboxylic Acids", pp. 80–121.

Kirk–Othmer, *Encyclopedia of Chemical Technology*, Third Edition, vol. 4, "Carboxylic Acids", pp. 814–871.

Dychdala, *Disinfection, Sterilization, and Predervtion*, Second Edition, "Acid–Anionic Surfactant Sanitizers", pp. 319–324.

Foegeding et al., *Disinfection, Sterilization, and Preservation*, Fourth Edition, "Chemical Food Preservatives", pp. 802–832.

Committee on Specifications, . . . , *Food Chemicals Codex*, Second Edition, pp. 12–14.

*Code of Federal Regulations*, Food and Drugs, Revised as of Apr. 1, 1991, pp. 311–318.

*Food Acidulants*, pp. 7, 13, 44 and Chapter 8, pp. 97–114 which discusses various aspects of acidulants.

Chemical Abstracts, vol. 111, No. 11 (Sep. 11, 1989), Abstract No. 95735r.

The Chemical Food News Guide, Oct. 7, 1991.

The Chemical Food News Guide, Jun. 26, 1989.

Chemical Abstracts, Abstract No. 95723k, "Study of Calcium Binding to Phosphoserine Residues of –Casein and Its Phosphopeptide (1–25) by $^{31}P$ NMR", vol. 111, pp. 609–610 (1989).

Chemical Abstracts, Abstract No. 166345q, "Disinfectant Compositions Containing Aqueous Lower Alcohol, Acidic Component, and Amino– or Ammonium–Based Microbicide", vol. 108, p. 549 (1988).

Pharmaceuticals, Abstract No. 32300p, "Germ-Killing Materials", vol. 102, p. 491 (1985).

Pharmaceuticals, Abstract No. 60796u, "Antibiotic and Mucolytic Compositions", vol. 70, p. 231 (1969).

SANITIZING COMPOSITIONS

This application is a continuation-in-part of U.S. patent application Ser. No. 07/989,507 filed Dec. 11, 1992, now U.S. Pat. No. 5,234,719.

FIELD OF THE INVENTION

The invention relates to microbicidal compositions for sanitizing inanimate surfaces. More specifically, the invention relates to microbicidal compositions which include an octanoic carboxylic acid and a sulfur containing compound as an antimicrobial agent. The composition is preferably safe for incidental human contact as well as food contact surfaces without requiring a post-sanitizing rinse. The microbicidal compositions of the invention are suitable for dairy farms, food and beverage processing plants, food preparation kitchens, food serving establishments, child-care, nursing-care and hospital-care applications, as well as for general utility in domestic households and institutions.

BACKGROUND OF THE INVENTION

The list of microbicidal agents has decreased due to their human toxicity and their detrimental effect on water supplies and the overall environment. Improving analytical capabilities to detect parts-per-billion levels in food, water and in the environment generally have raised important safety concerns about the application and misapplication of these chemicals. These issues have resulted in the banning of some antimicrobials, for example hexachlorophene; the retesting of others for animal toxicity, such as, the quaternary ammonium compounds; and, the increasing scrutiny of microbicidal species such as chlorine or hypochlorites which may form toxic halocarbons in effluent waters.

There has been a long felt need for antimicrobial agents which have a high degree of antimicrobial efficacy, and which are preferably safely used around sensitive areas while also posing no environmental incompatibility. Those antimicrobial agents which are lethal to microorganisms, however, are also toxic in varying degrees to humans and animals in that both higher and lower forms of life share at least some common metabolic pathways. Competitive inhibition, non-competitive inhibition, protein coagulation, oxidative and reductive action, blockage of enzyme systems are thought to be some of the mechanisms involved in the destruction of microorganisms.

Differentiation of antimicrobial "-cidal" or "-static" activity, the definitions which describe the degree of efficacy, and the official laboratory protocols for measuring this efficacy are important considerations for understanding the relevance of antimicrobial agents and compositions. Antimicrobial compositions may effect two kinds of microbial cell damage. The first is a truly lethal, irreversible action resulting in complete microbial cell destruction or incapacitation. The second type of cell damage is reversible, such that if the organism is rendered free of the agent, it can again multiply. The former is termed bactericidal and the latter, bacteriostatic. Sanitizers, disinfectants and tuberculocidal agents are, by definition, agents which provide bactericidal activity. In contrast, a preservative is generally described as inhibitory or bacteriostatic.

A sanitizer is an agent that reduces the number of bacterial contaminants to safe levels as judged by public health requirements. Practically, a sanitizer must result in 99.999% reduction (5 log order reduction) for given organisms as defined by *Germicidal and Detergent Sanitizing Action of Disinfectants*, Official Methods of Analysis of the Association of Official Analytical Chemists ("A.O.A.C."), paragraph 960.09 and applicable sections, 15th Edition, 1990 (EPA Guideline 91-2).

A disinfectant is an agent that kills all vegetative cells including most recognized pathogenic microorganisms. As such, it must pass a more stringent bactericidal test; the *A.O.A.C., Use Dilution Methods*, Official Methods of Analysis of the Association of Official Analytical Chemists, paragraph 955.14 and applicable sections, 15th Edition, 1990 (EPA Guideline 91-2).

A tuberculocide is a higher order disinfectant which is capable of killing all vegetative tuberculosis bacteria cells. Tuberculocidal activity is determined by *Tuberculocidal Activity of Disinfectants*, Official Methods of Analysis of the Association of Official Analytical Chemists, paragraph 965.12 and applicable sections, 15th Edition, 1990.

In contrast, a preservative is described as any agent that generally extends the storage life of perishable products such as food and non-food products by retarding or preventing deterioration of flavor, odor, color, texture, appearance, nutritive value, or safety. One method used for evaluating such materials is designated Minimum Inhibitory Method Concentration. Another procedure is entitled Zone of Inhibition. Preservatives, by definition, are therefore inhibitory substances added to food to prolong or enhance shelf-life. The principal differences between a preservative and a sanitizer are two-fold; 1) mode of action, a preservative prevents growth rather than killing microorganisms; and, 2) exposure time, a preservative has days to months. In contrast, a sanitizer must provide 99.999% kill (5 log order) within 30 seconds at nominal 20° C.

Ideally, a sanitizing agent or compound will possess several important properties in addition to its microbicidal efficacy. The sanitizer should be no-rinse after application, and have residual antimicrobial activity. Residual activity implies a film of sanitizing material which will continue to have antimicrobial effect if the treated surface is contaminated by microorganisms during a storage or lag period. The sanitizer should be odor free to prevent transfer of undesirable odors onto contact surfaces or articles with which it otherwise comes into contact. The sanitizer should be composed of ingredients which will not affect food if incidental contact or contamination occurs, nor affect humans should incidental ingestion result. In addition, the sanitizer should be composed of naturally occurring or innocuous ingredients, which are chemically compatible with the environment and cause no concern for toxic residues in downstream water.

Previously, certain compositions have been recognized as effective in providing sanitizing, disinfecting, and preservative effects. For example, U.S. Pat. No. 4,404,040 to Wang discloses the sanitizing properties of short chain fatty acids formulated with an ionic hydrotrope-solubilizer and compatible acids. U.S. Pat. No. 4,647,458 to Ueno et al, discloses bactericidal compositions comprising a large concentration of ethyl alcohol, an organic acid, and an inorganic acid.

Moreover, U.S. Pat. No. 3,915,633 to Ramachandran, discloses a prewash composition for treating fabrics which includes an organic acid such as citric acid and either a nonionic or an anionic surfactant. U.S. Pat. No. 3,867,300 to Karabinos, discloses bactericidal compositions presumably for controlling the spread of nosocomial infections in hospitals consisting of an aliphatic monocarboxylic acids, and nonionic surfactants. U.K. Patent Application GB 2,103,089A to Kimberly Clark discloses the use of carboxylic acids as virucides. U.S. Pat. No. 4,715,980 to Lopes et al, discloses an antimicrobial concentrate composition containing a dicarboxylic acid, a solubilizer, an acid, and a diluent. U.S. Pat. No. 3,650,965 to Cantor et al, discloses clean-in-place detergent solutions for treating milk and food processing equipment based on two different nonionic surfactants.

U.S. Pat. No. 4,002,775 to Kabara discloses the use of mono-esters of twelve carbon aliphatic fatty acids and polyols. European Patent Application No. 87303488 to Kabara discloses antimicrobial preservative compositions of glycerol mono esters, preferably monolaurin and fatty acids. However, similar to Wang and Ueno et al, the disclosure in these publications is not specific to $C_8$ acids and further does not discuss the antimicrobial activity of these acids in conjunction with their use with certain adjuvants.

Currently, products used for sanitizing operations include strong oxidizing agents such as peracetic acid, iodophors, sodium hypochlorite and related n-chloro compounds such as chloro isocyanurates, quaternary ammonium compounds and the like. While these are no rinse sanitizers, they are not ideal for one reason or another.

Peracetic acid, iodophors and chlorine based sanitizers are either decomposed or lost by evaporation when a film of sanitizer is left on the contact surface and allowed to dry. Thus no residual activity remains on the intended surface. Residual activity is necessary to provide continued antimicrobial effect if the surface is contaminated by microorganisms during storage.

Quaternary ammonium compounds (QAC) have an excellent residual quality as they are stable and increase in concentration as the solvent (water) evaporates. Unfortunately, for many uses, this residue may carry into sensitive areas which do not tolerate QAC residues. For example, trace amounts of QAC in substances such as milk, inhibits the starter culture which produces lactic acid and flavor resulting in the curdling of milk protein.

Acid based sanitizers often contain foam control agents or surfactant couplers which are also incompatible in sensitive areas. Moreover, carboxylic acid based sanitizers often have undesirable organoleptic properties exemplified by a "goat-like" odor. The longer chain fatty acids have limited solubilities in water and require thorough rinsing with potable water before contact of the sanitized surface to avoid imparting odors or flavors to articles contacting the surface.

While all these compositions are excellent sanitizers, many of their ingredients are not applicable or otherwise compatible with contact sensitive surfaces. Consequently, these current, commercially successful products have not been designed for user safety, misapplication or environmental compatibility. Thus a sanitizing agent which specifically addresses these issues would possess utility and uniqueness not found in heretofore described sanitizers.

SUMMARY OF THE INVENTION

The invention is based on the surprising discovery of an antimicrobial composition which is capable of providing sanitizing and disinfecting antimicrobial efficacy as well as tuberculocidal activity. We have found that octanoic acid and when combined with various sulphur containing compounds have an unexpected level of antimicrobial properties in comparison to other antimicrobial compositions.

The composition of the invention generally comprises a carrier and an antimicrobial agent of octanoic carboxylic acid and a sulfur compound. Optionally, the invention may also contain a variety of formulatory or application adjuvants. The invention also comprises concentrate compositions and methods of sanitizing and disinfecting using the antimicrobial composition of the invention.

The claimed composition eliminates the potential for recontamination of sanitized surfaces by potable water which may be safe to drink but may contain microorganisms. This is particularly important in environments such as, for example, where there is a delay between sanitizing operation and use of food preparation equipment. In cases where equipment remains wet between uses, contaminating organisms may grow freely. Airborne contamination may also be retarded by the invention by retention of compositional residue on surfaces. Especially in the presence of moisture, this residue will continue its antimicrobial action. When residual amounts of the invention are retained on the surface of application, continued sanitizing action will occur in the face of exposure to contaminating splash and spray.

The invention is also applicable to closed systems such as pipelines and holding tanks which may be difficult to completely drain. When used, the invention will continue to effectively destroy any microorganisms which might be present without creating risk of harmful food contamination or environmental contamination.

DETAILED DESCRIPTION OF THE INVENTION

The invention comprises a composition capable of imparting sanitizing and disinfecting antimicrobial efficacy as well as tuberculocidal activity. The composition may also comprise an acidulant along with any variety of other formulatory or application adjuvants.

The invention also comprises concentrate and use dilution formulations which may take the form of liquid solutions, gels, as well as impregnated sponges, towelettes, aerosol and pump sprays or solids. The invention further comprises methods of sanitizing and disinfecting using the composition of the invention.

I. Antimicrobial Agent

The composition of the invention generally comprises an antimicrobial agent.

The invention is based on a discovery that a specific carboxylic acid, octanoic acid when combined with a sulfur containing compound, surprisingly provides extraordinary sanitizing, if not tuberculocidal, disinfecting, antimicrobial efficacy.

Generally, the antimicrobial agent of the invention functions to sanitize or disinfect the intended surface of application. Further, the composition of the invention also provides tuberculocidal activity. The antimicrobial agent of the invention is intended to provide tuberculocidal, sanitizing or disinfecting antimicrobial activity upon application to the intended surface, leaving a residue which upon contact with foodstuffs will not contaminate or otherwise preclude ingestion of the prepared food.

Generally, the composition of the invention is applicable to all food collection, process, preparation and serving environments and facilities as well as other contact sensitive areas such as day and child care facilities, nursing homes and other health care facilities, and domestic households.

Thus, a sanitizer and disinfectant which is excellent microbiocidally, does not require a post-sanitizer rinse, imparts no off-flavor or odor to food, possess residual activity, and minimizes the potential for acute and chronic human toxicity and environmental contamination fulfills a need not currently met by presently available sanitizers.

The antimicrobial agent of the invention comprises a carboxylic acid system of octanoic acid and derivatives thereof combined with a sulfur containing compound. Carboxylic acids are characterized by the presence of one or more carboxyl groups which generally have the structure:

Carboxylic acids as a group are usually considered to be relatively weak acids.

Even in view of the weakness of these acids, we have found that one carboxylic acid provides unique antimicrobial efficacy despite this classification. The antimicrobial agent of the invention consists of octanoic acid as well as, octanoic acid esters, or salts. Octanoic acid also known as caprylic acid, occurs naturally as glycerides and may generally be derived by saponification and subsequent distillation of coconut oil. Octanoic acid is generally an oily liquid having a boiling point of 239.7° C., a melting point of 16.7° C. and a density of 0.910 (at 20° C.). Octanoic acid is known by the formula:

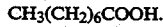

In addition to antimicrobial efficacy resulting from simple octanoic acid, antimicrobial efficacy may also result from octanoic acid esters, or salts. Specifically, the carboxylic acid of the invention may also be derivatized into the form of a carboxylic acid ester, or carboxylic acid salt. Further, as with all carboxylic acids, industrial grades of octanoic acid may also comprise minor proportions of other carboxylic acids as impurities.

Generally, the linear carboxylic acid of the invention may also take the form of a salt formed by reaction with an alkaline substance most commonly from oxides, hydroxides or carbonates of monovalent and divalent metals in Periodic Groups IA and IIA; but, also with basic positive complexes such as the ammonium radical and organic amine moieties.

The carboxylic acid of the invention may also comprise an ester derivative of that carboxylic acid. Common ester derivatives of carboxylic acids are those wherein the hydroxy group is replaced by an alkoxy group which may comprise any number of different alkyl moieties which do not impede the efficacy of the octanoic acid compound.

The principal types of esters result from reaction with monohydric alcohols, polyhydric alcohols and ethylene or propylene oxide. The most common monohydric alcohols used are the simple alkyl alcohols such as methyl, ethyl, propyl, isopropyl, and the like. The most common polyhydric alcohols include polyethylene glycol, glycerol, sorbitol, and certain carbohydrates such as sucrose.

Accordingly, the octanoic carboxylic acid of the invention may comprise any number of acid salts, acid esters, and the like. Preferably, the compound used in the invention is octanoic acid or an octanoic acid salt or an octanoic acid ester.

Generally, depending on whether the composition is a use dilution or concentrate formulation, octanoic acid may be present in concentrations ranging generally from about 0.01 wt-% to about 45 wt-% preferably from about 0.03 wt-% to about 40 wt-%, and most preferably from about 0.05 wt-% to about 35 wt-%.

The concentration figures detailed above for octanoic acid are presented as guidelines. Actual concentrations vary depending upon the carrier used in the formulation, whether aqueous, organic, inorganic or mixtures thereof; the overall nature of the formulation, whether neat solution, liquid concentrate, or aerosol, dispersion, emulsion, gel, or solid; the delivery and application method; and, the compositional adjustments necessary for physical and chemical stability during storage or use in adverse environments.

Additionally, the antimicrobial agent of the invention also comprises a compound containing sulfur. Sulfur compounds and especially compounds such as sulfonates, and sulfates, among others, provide a tuberculocidal, sanitizing and disinfecting antimicrobial character when combined with octanoic acid and derivatives thereof. Further, these sulfur compounds may also function to increase acidity, as well as provide surface activity and coupling within the composition. Generally, this agent may comprise any compound, surfactant, polymer, or mixture thereof containing sulfur. Preferably the sulfur compound comprises an organic sulfonic acid moiety or sulfuric acid ester to provide antimicrobial efficacy, acidity, and surface activity.

Generally, the sulfur compound may comprise an aliphatic, aromatic, or alicyclic structure and derivatized combinations thereof which have been subjected to sulfonation, or sulfation reactions. In sulfonation, a new C—S bond is created and a $SO^-_3$ group is introduced into an organic molecule to provide a derivative with a C—$SO^-_3$ linkage, a grouping known as a sulfonate which may remain protonated (sulfonic acid), or be neutralized with base (sulfonic acid salts). Sulfation results from any process of introducing an $SO_3$ group into an organic compound by forming a C—O or O—S of the C—O—S bond sequence. The reaction product, a sulfate, exhibits the characteristic —C—O—$SO^-_3$ configuration.

Generally, in the context of the claimed invention, the acid form of a sulfonated or sulfated compound or polymer is preferred. Compounds which may be sulfonated or sulfated for use in accordance with the invention include the acid and various salt derivatives of sulfonated paraffins, sulfonated olefins, sulfonated lignins, sulfonated mono and polycarboxylic acids and alcohol esters of these acids; and, sulfonated alicyclic, aromatic, and alkylaryl moieties; also, the acid and corresponding salt compounds of sulfated alcohols and ether alcohols; sulfated glycerol esters of fatty acids; and products obtained by sulfation of saturated, unsaturated and hydroxy fatty acids and natural fats and oils containing their glycerides, as well as monohydric and polyhydric alcohol esters of these acids, among others.

One preferred class of compounds are alkyl-aryl sulfonates such as alkyl benzene sulfonates.

Specifically preferred compounds are aromatic sulfonate compounds such as alkyl benzene sulfonates, decanoic benzene sulfonates, dodecanoic or dodecyl benzene sulfonates, tetradecanoic benzene sulfonates, and hexadecanoic benzene sulfonates, and mixtures thereof. These compounds may also be used in their acid form as sulfonic acid compounds.

The most preferred sulfur compound has been found to be dodecyl benzene sulfonic acid as it is a very strong acid affecting protonation of weak fatty acids such as octanoic acid, and is of itself a microbiocide as well as a good surfactant.

Generally, depending on whether the composition is a used dilution or concentrate formulation, octanoic acid may be present in concentrations ranging generally from about 0.01 wt-% to 45 wt-%, preferably from about 0.03 wt-% to 40 wt-%, and most preferably from about 0.05 wt-% to 35 wt-%.

II. Carrier

The antimicrobial composition of the invention also comprises a carrier. The carrier within this composition functions to transport the antimicrobial agents to the intended surface of application and define the forms of the composition whether liquid, semi-solid such as a gel, or solid. Moreover, depending upon the nature of the carrier, this constituent may be used to maintain the antimicrobial agent on the intended surface for an extended period of time in the form of a film or residue after application. Keeping these functions in mind, the carriers useful in the invention should preferably maintain and not obscure the efficacy of the antimicrobial agent.

The composition of the invention may take the form of a neat solution or liquid concentrate, dispersion, emulsion, aerosol, gel, or solid. The invention may also take the form of a liquid impregnated sponge or towelette where the carrier comprises, in addition to a liquid, a chemically inert carrier such as a fabric or sponge. Accordingly, the choice of any carrier useful in the invention will depend somewhat on the intended form and intended use application of the final composition. If the invention takes the form of a solution, dispersion, gel, emulsion, aerosol, or solid, useful carriers include water or aqueous systems as well as organic or inorganic based carriers, or mixtures thereof.

Organics which have been found especially useful include simple alkyl alcohols such as ethanol, isopropanol, n-propanol and the like. Polyols are also useful carriers in accordance with the invention, including propylene glycol, polyethylene glycol, glycerol, sorbitol and the like. Any of these compounds may be used singly or in combination with another organic or inorganic carrier or, in combination with water, or in mixtures thereof.

If organic, the carrier may also comprise any number of surfactants or surfactant combinations. Surface active agents which have been found as useful carrier in accordance with the invention include anionic and nonionic agents such as, for example, propylene glycol esters, glycerol esters, polyoxyethylene glycerol esters, polyglycerol esters, sorbitan esters, polyoxyethylene sorbitan esters, sucrose esters, polyethylene glycol esters, polyoxyethylene-polyoxypropylene ether adducts, dioctyl sodium succinate, stearoyl lactylate, and esters of acetylated, lactylated, citrated, succinylated or diacetyl tartarated glycerides.

Preferred surfactants include nonionic surfactants having a mixture of polyoxyethylene and polyoxypropylene moieties. Specifically, one nonionic surfactant found to be especially preferred is a polyoxyethylene, polyoxypropylene block copolymer having about 240 to 280 moles of ethoxylation and about 45–65 moles of propoxylation.

If the invention is formulated as a solid, the carrier may be selected from any organic or inorganic compound which imparts a solid form and hardness to the composition of the invention either by a hot-melt, pour-cast process, by extrusion, or by compression. Typical organic ingredients which may be used in the solid antimicrobial composition of the invention to harden this composition include amides, polyols, and certain nonionic and anionic surfactants.

For example, stearic monoethanol amide, stearic diethanol amide and urea have been found to effectively result in the formulation of a hardened product. Moreover, polyols such as polyethylene glycol, and polyhydric sugar alcohols such as mannitol and the like or mixtures thereof have all been found to impart a hardened but soluble character when combined in the composition of the invention.

Surfactants useful in this invention as a hardening agent and carrier are solid, generally high melting analogs of nonionics and anhydrous metallic salts of anionic surfactants which include alkyl and dialkyl phenol ethoxylates, linear alkyl alcohol ethoxylates, polyalkoxide polymers of ethanolamines, ethylene oxide/propylene oxide block copolymers, polyalkylene oxide block polymers of ethylene diamine, glycerol esters, polyoxyethylene glycerol esters, polyglycerol esters, sorbitan esters, polyoxyethylene sorbitan esters, sucrose esters, polyethylene ethers, dioctyl sodium sulfo succinate, stearoyl lactylate, and complex esters such as acetylated, lactylated, citrated, succinylated, and diacetyl tartarated glycerides.

Other compositions which may be used as hardeners within the composition of the invention include sugars, and modified starches or cellulosics which have been made water soluble through acid or alkaline treatment processes.

Inorganics which may be used in forming the hardened antimicrobial composition of the invention include salts formed of periodic Groups IA and IIA metals, as well as ammonium, with the corresponding negative ions or radicals of mineral acids such as chloride ions, carbonate ions, nitrate ions, phosphate ions, and sulphate ions as well as their respective hydrates, protic salt forms, or in the case of phosphates, the various condensate species.

Generally, any type of carrier capable of solidifying the antimicrobial agent may be used in accordance with the invention. To this end, urea, Pluronic ™ F-108 and polyethylene glycol have been found to be beneficial solidifying agents.

Generally, the carrier comprises a large portion of the composition of the invention. Here again, the carrier concentration and type will depend upon the nature of the composition as a whole, the environment of storage and method of application including the concentration of antimicrobial agent, among other factors. Notably, the carrier should be chosen and used at a concentration which does not inhibit the antimicrobial efficacy of the active in the present composition.

III. Adjuvants

Alternatively, the composition of the invention may also comprise any number of adjuvants. Depending on the benefits provided by the adjuvant, adjuvants may partially or wholly displace the carrier in the composition. Generally, in accordance with the invention, there may be included within this composition formulatory adjuvants or adjuvants which assist in the application of the invention with respect to performance, form, aesthetics, and stability when stored or used within adverse conditions.

Formulatory adjuvants include coupling agents, solubilizers, or hydrotropes used to maintain the storage stability of the present composition as well as solubilizing the antimicrobial agent of the invention.

This function may be accomplished exclusively by the carrier whether aqueous, organic, inorganic or a mixture thereof. However, in situations which require formulation of a concentrated antimicrobial system, an additional organic agent may be introduced into the system to facilitate solubilization of the antimicrobial agent.

To this end, any number of organic coupling agents may be used including monofunctional and polyfunctional alcohols. Those coupling agents which have been found most useful include linear alkyl alcohols such as, for example, ethanol, isopropanol, and the like polyfunctional organic alcohols include glycerol, hexylene glycol, polyethylene glycol, propylene glycol, sorbitol and the like. Generally, depending on whether the composition is in the form of a concentrate or use dilution formulation, the concentration of these adjuvant compounds, when used in these capacities, ranges from about 0 wt-% to about 99 wt-%, preferably from about 0.1 wt-% to about 97 wt-%, and most preferably from about 0.15 wt-% to about 95 wt-%.

The invention may also comprise one or more acidulants useful in lowering the pH of the present composition. Acidulants useful in the present composition include lactic acid, phosphoric acid, sulfuric acid, sulfamic acid, adipic acid, tartaric acid, succinic acid, acetic acid, propionic acid, citric acid, malic acid, or mixtures thereof. Further it has been found that a use dilution solution pH ranging from about 1.3 to 4, preferably from about 1.4 to 3, and most preferably from about 1.5 to 2.5 provide the most desirable antimicrobial efficacy.

The composition of the invention may also comprise surface tension altering constituents such as various anionic and nonionic surfactants. These surfactants may be used to maintain constituents in solution over various temperature gradients as well as altering the wettability and cleaning capabilities of the composition of the invention to any variety of surfaces. Any number of surfactants or combinations thereof may be used in accordance with the invention.

The surface active agents which have been found useful in accordance with the invention include anionic and nonionic agents including, for example, propylene glycol esters, glycerol esters, polyoxyethylene glycerol esters, polyglycerol esters, sorbitan esters, polyoxyethylene sorbitan esters, sucrose esters, polyethylene glycol esters, polyoxyethylene-polyoxypropylene ether adducts, dioctyl sodium succinate, stearoyl lactylate, and complex esters such as acetylated, lactylated, citrated, succinylated, or diacetyl tartarated glycerides.

One class of surfactants which has been found especially useful in formulating the various embodiments of the present composition includes nonionic surfactants which have a mixture of hydrophilic and hydrophobic character. Generally, a mixture of hydrophilic and hydrophobic character in the surfactants has been found particularly useful in accordance with the invention and is created by the presence of polyoxyethylene and polyoxypropylene moieties.

Nonionic surfactants which are especially useful include those surfactants having about 5–300 moles of ethoxylation and about 10–80 of propoxylation. One surfactant which has been found most useful is Pluronic ™ F-108 which is a nonionic surfactant generally defined as a polyoxyethylene, polyoxypropylene block copolymer having about 240 to 280 moles of ethoxylation and about 45 to 65 moles of propoxylation, sold by BASF-Wyandotte Company Inc. We have found that BASF-Wyandotte Company Inc. Pluronic F-108 is useful for formulating solid and gel concentrates, and Pluronic L-44, (having about 5 to 15 moles of EO and 10 to 30 moles of PO), is useful for formulating liquid concentrates.

Surface tension altering constituents of the invention may be used in the present composition, regardless of form or application, depending on whether the composition is a concentrate or use dilution formulation, in concentrations ranging from about 0 wt-% to 60 wt-%, preferably from about 0.01 wt-% to 50 wt-%, and most preferably from about 0.02 wt-% to 40 wt-% depending on whether the surfactant is present for wetting, detergency, or coupling.

Here again, the concentration and type of surfactant used should not inhibit the antimicrobial action of the active within the invention. The concentration of surfactant adjuvant may also vary depending upon the nature of the formulatory composition as a whole, the concentration of antimicrobial agent, as well as the storage environment and method of application among other factors.

As the invention may take the form of a spray, either pump or aerosol, adjuvants which may be used with the carrier in the invention include propellants. Any number of propellants may be used including n-butane, isobutane and propane, among others. The concentration of propellant will generally range from about 3 wt-% to about 25 wt-%, preferably from about 4 wt-% to about 20 wt-%, and most preferably from about 5 to about 15 wt-%.

The composition of the invention may also comprise adjuvants which facilitate the application of this composition through various vehicles. Specifically, the composition of the invention is useful as an antimicrobial agent in hand creams, sponges, towelettes, hand cleansers, dips, sprays and washes among other uses. Accordingly, the composition of the invention may comprise any number of conditioners or emollients, humectants, perfumes, thickeners, opacifiers or particulates, colorants or dyes, cleansers or other agents useful in facilitating the application of the composition of the invention to its intended application.

Table 1 provides a general directory of guideline concentrations for the various compositional forms of the invention.

TABLE 1

|  | USEFUL | PREFERRED | MOST PREFERRED |
|---|---|---|---|
| USE-DILUTION CONCENTRATION RANGES (wt-%) | | | |
| ANTIMICROBIAL AGENT | 0.02–1.0 | 0.06–0.7 | 0.1–0.4 |
| OCTANOIC ACID | 0.01–0.5 | 0.03–0.35 | 0.05–0.2 |
| SULFUR COMPOUND | 0.01–0.5 | 0.03–0.35 | 0.05–0.2 |
| CARRIER | 54.98–99.98 | 64.94–99.84 | 74.9–99.75 |
| ADJUVANTS | 0–45 | 0.1–35 | 0.15–25 |
| pH | 1.3–4 | 1.4–3 | 1.5–2.5 |
| LIQUID CONCENTRATE RANGES (wt-%) | | | |

TABLE 1-continued

|  | USEFUL | PRE-FERRED | MOST PREFERRED |
|---|---|---|---|
| ANTIMICROBIAL AGENT | 1–90 | 3–80 | 5–70 |
| OCTANOIC ACID | 0.5–45 | 1–40 | 1.5–35 |
| SULFUR COMPOUND | 0.5–45 | 1–40 | 1.5–35 |
| CARRIER | 0–99 | 0–95 | 0–91 |
| ADJUVANTS | 0–99 | 2–97 | 4–95 |
| pH (USE-DILUTION) | 1.3–4 | 1.4–3 | 1.5–2.5 |
| SOLID CONCENTRATE RANGES (wt-%) | | | |
| ANTIMICROBIAL AGENT | 1–60 | 2–50 | 3–40 |
| OCTANOIC ACID | 0.5–30 | 1–25 | 1.5–20 |
| SULFUR COMPOUND | 0.5–30 | 1–25 | 1.5–20 |
| CARRIER | 40–99 | 48–96 | 56–93 |
| ADJUVANT | 0–54 | 2–50 | 4–41 |
| pH (USE-DILUTION) | 1.3–4 | 1.4–43 | 1.5–2.5 |
| GEL COMPOSITION RANGES (wt-%) | | | |
| ANTIMICROBIAL AGENT | 1–50 | 2–40 | 3–30 |
| OCTANOIC ACID | 0.5–25 | 1–20 | 1.5–15 |
| SULFUR COMPOUND | 0.5–25 | 1–20 | 1.5–15 |
| CARRIER | 30–94 | 38–91 | 47–88 |
| ADJUVANTS | 5–70 | 7–60 | 9–50 |
| pH (USE DILUTION) | 1.3–4 | 1.4–3 | 1.5–2.5 |

The concentrations provided above generally reflect a ratio of octanoic acid to the sulfur compound of about 1:1. This ratio may range from about 1:0.5 to 10, preferably about 1:0.5 to 2.

In use we have found that a dilution rate which results in an active concentration of ranging from about 500 ppm to 1500 ppm, preferably about 750 ppm to 1250 ppm, and most preferrably 900 ppm to 1100 ppm of each of octanoic acid and sulfur containing compounds has been found useful.

The liquid concentrate may comprise water in the form of carrier ranging from about 0 wt-% to 70 wt-%, preferrably from about 15 wt-% to 70 wt-%, most preferrably from about 30 wt-% to 70 wt-% as a percentage of the total composition. The gel concentrate may comprise water in the form of carrier ranging from about 0 wt-% to 80 wt-%, preferrably from about 15 wt-% to 60 wt-%, and most preferrably about 25 wt-% to 40 wt-% as a percentage of the total composition.

WORKING EXAMPLES

Following below are formulatory, stability, application and microbiological working examples using the composition of the invention. While the invention is exemplified by the working examples, it is not limited to the examples shown hereinafter.

WORKING EXAMPLES 1–40

Formulatory working examples, working examples 1–40, were prepared by combining the antimicrobial of the invention with various constituents to show compatibility as well as antimicrobial efficacy.

Generally, nonionic coupling agents were thought not to be compatible with various fatty acid compounds such as octanoic acid. Contrary to this general statement, the working examples of Table 2 show that octanoic acid when combined into the composition of the invention are compatible with nonionics such as Pluronic ™ F-108 (manufactured by BASF/Wyandotte); (all concentrations are in wt-%). This unexpected compatibility, exceeding 1 wt-% nonionic in use dilution, is important in that coupling agents may be used to stabilize the fatty acid against phase separation at extreme temperature. This is especially relevant when a concentrated sanitizer or disinfectant is desired. Moreover, this level of nonionic surfactant was shown to not affect the antimicrobial efficacy of the composition (see Table 3).

TABLE 2

| COMPONENT | 1 | 2 | 3 | 4 | 5 | 6 | 7 | 8 |
|---|---|---|---|---|---|---|---|---|
| Octanoic Acid | 32.00 | 32.00 | 28.57 | 29.63 | 30.19 | 30.32 | 32.00 | 30.48 |
| LAS* (97% w/v) | 20.00 | 20.00 | 17.86 | 18.52 | 18.87 | 18.95 | 20.00 | 19.05 |
| Distilled Water | 20.00 | 34.00 | 33.93 | 39.81 | 40.57 | 40.73 | 43.00 | 40.95 |
| Hexylene Glycol | 28.00 | 14.00 | 6.25 | 7.41 | 5.66 | | | 4.76 |
| Nonylphenol Ethoxylate (9.5 moles EO) | | | 13.39 | | | | | |
| Pluronic ™ F-108** | | | | 4.63 | | | | |
| Pluronic ™ F-38** | | | | | 4.72 | | | |
| Pluronic ™ L-44** | | | | | | 10.00 | | |
| Phosphate ester (acid) of a $C_{10-14}$ alcohol ethoxylate (60 moles EO) | | | | | | | 5.00 | |
| Alcohol ethoxylate ($C_{10-14}$ 20 moles EO) | | | | | | | | 4.76 |

| COMPONENT | 9 | 10 | 11 | 12 | 13 | 14 | 15 | 16 |
|---|---|---|---|---|---|---|---|---|
| Octanoic Acid | 31.37 | 25.60 | 24.33 | 22.82 | 24.38 | 24.38 | 23.46 | 24.38 |
| LAS* (97% w/v) | 19.61 | 10.00 | 9.50 | 8.92 | 9.52 | 9.52 | 27.49 | 9.52 |
| Distilled Water | 42.16 | 49.40 | 46.96 | 44.04 | 47.05 | 47.05 | 36.11 | 47.05 |
| Hexylene Glycol | | | 14.46 | | | | 12.94 | |
| Nonylphenol Ethoxylate (9.5 moles EO) | | | | | 4.76 | | | |
| Nonylphenol Ethoxylate (15 moles EO) | 6.86 | | | | | | | |
| Pluronic ™ F-108 | | 5.00 | 4.75 | 4.46 | | 4.76 | | 4.76 |
| Sodium Lauryl Sulfate | | 5.00 | | | | | | |
| Propylene Glycol | | 5.00 | | 19.76 | | | | |
| Sodium Xylene Sulfonate | | | | | 14.29 | | | |
| Urea | | | | | | 14.29 | | |
| Lactic Acid | | | | | | | | 14.29 |

| COMPONENT | 17 | 18 | 19 | 20 | 21 | 22 | 23 | 24 |
|---|---|---|---|---|---|---|---|---|
| Octanoic Acid | 24.38 | 25.60 | 25.60 | 25.60 | 24.98 | 26.67 | 24.38 | 25.60 |

TABLE 2-continued

| | (wt-%) | | | | | | | |
|---|---|---|---|---|---|---|---|---|
| LAS* (97% w/v) | 19.05 | 20.00 | 20.00 | 20.00 | 12.20 | 12.50 | 19.05 | 12.00 |
| Distilled Water | 42.28 | 39.40 | 39.40 | 39.40 | 55.01 | 49.38 | 42.29 | 47.40 |
| Hexylene Glycol | | 10.00 | 10.00 | | | | | |
| Butyl Carbitol | | | | 2.93 | | | 9.52 | 10.00 |
| Methyl Carbitol | | | | | 6.25 | | | |
| Pluronic™ F-108** | | 5.00 | | | | | 4.76 | 5.00 |
| Pluronic™ F-38** | | | 5.00 | 5.00 | 4.88 | 5.20 | | |
| Pluronic™ L-44** | | | | 10.00 | | | | |
| Lactic Acid | 14.29 | | | | | | | |

| COMPONENT | 25 | 26 | 27 | 28 | 29 | 30 | 31 | 32 |
|---|---|---|---|---|---|---|---|---|
| Octanoic Acid | 26.95 | 25.60 | 25.60 | 25.60 | 24.62 | 25.60 | 25.60 | 25.60 |
| LAS* (97% w/v) | 12.63 | 20.00 | 12.00 | 12.00 | 19.23 | 25.00 | 12.00 | 20.00 |
| Distilled Water | 49.90 | 41.90 | 49.90 | 42.40 | 41.72 | 34.40 | 42.40 | 44.40 |
| Hexylene Glycol | | 10.00 | 10.00 | 10.00 | 4.81 | 5.00 | 10.00 | 5.00 |
| Isopropanol (91% w/v) | 5.26 | | | | | | | |
| Pluronic™ F-108** | 5.26 | 2.50 | 2.50 | | | | | |
| Pluronic L™-44** | | | | 10.00 | 9.62 | 10.00 | | 5.00 |
| Ecolab LF071 (BLOCK CO-POLYMER (mw 1400)) | | | | | | | 10.00 | |

| COMPONENT | 33 | 34 | 35 | 36 | 37 | 38 | 39 | 40 |
|---|---|---|---|---|---|---|---|---|
| Octanoic Acid | 12.80 | 12.80 | 12.80 | 6.40 | 25.60 | 25.60 | 25.60 | 12.80 |
| LAS* (97% w/v) | 12.80 | 20.00 | 12.80 | 12.80 | 25.00 | 25.00 | 25.00 | 12.80 |
| Distilled Water | 64.40 | 57.20 | 57.40 | 67.80 | 34.40 | 34.40 | 33.40 | 56.40 |
| Hexylene Glycol | | | 12.00 | 8.00 | 5.00 | 5.00 | 6.00 | 13.00 |
| Pluronic L™-44** | 10.00 | 10.00 | 5.00 | 5.00 | 10.00 | | 10.00 | 5.00 |
| Pluronic™ L-35** | | | | | | 10.00 | | |

| COMPONENT | 41 | 42 |
|---|---|---|
| Octanoic Acid | 6.40 | |
| LAS* (97% w/v) | 12.80 | 25.00 |
| Distilled Water | 66.80 | 59.00 |
| Hexylene Glycol | 9.00 | 6.00 |
| Pluronic L™-44** | 5.00 | 10.00 |

(*Linear alkyl sulfonate)
(**Nonionic surfactants sold by BASF/Wyandotte)

TABLE 3

| Working Examples | Concentration | Proskauer-Beck* | Kirshners* | Middlebrook* |
|---|---|---|---|---|
| 39 | 1 oz/2 gal | 10/10 | 10/10 | 10/10 |
| 39 | 2 oz/3 gal | 10/10 | 10/10 | 10/10 |
| 42 | 1 oz/2 gal | 10/10 | 10/10 | 10/10 |
| 42 | 2 oz/3 gal | 10/10 | 10/10 | 10/10 |
| Control 1 (phenol) | 1:50 | 10/10 | 10/10 | 10/10 |
| Control 2 (phenol) | 1:70 | 8/10 | 10/10 | 9/10 |

The results indicate tuberculocidal efficacy is being achieved with a ten minute exposure time using either the 1 ounce per 2 gallons or 2 ounces per 3 gallons dilution.
*(# Negative Tubes/# Tubes Tested)
[1]Tuberculocidal Activity Disinfectants, Official Methods of Analysis of Official Analytical Chemists, Paragraph 969.12 and applicable sections, 15 Edition, 1990.

EXAMPLES 43-44

An A.O.A.C. Sterilant Test was performed on the formulations shown in Table 4A against *C. sporogenies* on silk sutures at a temperature of 80° C. with a 2.5 minute exposure time. Products were prepared in 100 ppm hard H₂O at concentrations of 3, 4, 5, 6, & 7%. Results are as follows:

TABLE 4A

| | (wt-%) | |
|---|---|---|
| COMPONENT | EXAMPLE 43 (wt-%) | EXAMPLE 44 |
| Octanic Acid | 32.0 | 25.6 |
| Pluronic™ F-108** | 19.2 | |
| Lactic Acid (88 w/v) | 48.8 | |
| Pluronic™ L-44** | | 10.0 |
| Dodecyl Benzene Sulfonic Acid (97% w/v) | | 25.0 |
| | | 33.4 |
| Distilled Water | | 6.0 |
| Hexylene Glycol | | |

TABLE 4B

| | (wt-%) | | |
|---|---|---|---|
| Example | Conc. (wt-%) | Primary Growth Tube | Secondary Tube Growth |
| 43 | 3% | 17/20 | 16/20 |
| | 4% | 20/20 | 19/20 |
| | 5% | 20/20 | 20/20 |
| | 6% | 20/20 | 20/20 |
| | 7% | 20/20 | 20/20 |
| 44 | 4% | 20/20 | 20/20 |
| | 5% | 20/20 | 20/20 |
| | 6% | 20/20 | 20/20 |

**Pluronics™ are EO/PO block copolymers of BASF/Wyandotte

TABLE 5

| | (Wt-%) | | | | |
|---|---|---|---|---|---|
| COMPONENTS (wt-%) | Aerosol | Hard Surface Wipes | Hand Wipes | Udder Wipe Sanitizing | Udder Prewipe |
| Deionized Water | 72.835 | 76.60 | 72.85 | 69.75 | 78.75 |
| Ethanol | 17.100 | 18.00 | 18.00 | 18.00 | 14.00 |
| Octanoic Acid | 0.143 | 0.15 | 0.15 | 0.15 | 0.10 |
| Lactic Acid | 0.143 | 0.15 | 1.00 | 0.50 | 0.15 |
| Citric Acid | | | 3.00 | 3.50 | |
| Propylene Glycol | 4.750 | 5.00 | 5.00 | 5.00 | 5.00 |
| Glycerol USP | | | | 3.00 | 2.00 |
| Pluronic™ F-108 | 0.029 | 0.10 | | 0.10 | |
| Propellant A-31* | 5.000 | | | | |

(Isobutane)

The above specification, examples and data provide a complete description of the manufacture and use of the composition of the invention. Since many embodiments of the invention can be made without departing from the spirit and scope of the invention, the invention resides in the claims hereinafter appended.

We claim as our invention:

1. A method of using an antibacterial composition, said method comprising the steps of:
   (a) providing an antimicrobial composition consisting essentially of a major portion of carrier and an effective tuberculocidal amount of octanoic acid, an octanoic acid ester or salt thereof, and a sulfur containing compound; said compound selected from the group consisting of an alkyl sulfate or sulfonate, an aryl sulfate or sulfonate, an alkylaryl sulfate or sulfonate, and mixtures thereof, at a ratio of about 1.05–10 of octanoic acid to sulfur compound and at a pH of about 1.3 to 4.0; and
   (b) applying said composition to the intended surface for at least ten minutes.

2. The method of claim 1, comprising the step of wiping said composition from said surface wherein said composition results in a noncontaminating residue.

3. A use dilution antimicrobial composition consisting essentially of a major portion of carrier selected from the group consisting of an aqueous solvent, an organic monofunctional alcohol, an organic polyfunctional alcohol and mixtures thereof; an antimicrobial consisting of about 0.01 wt-% to 0.50 wt-%, based on the composition as a whole, of octanoic acid, an octanoic acid ester or salt thereof, and about 0.01 wt-% to 0.50 wt-%, based on the composition as a whole, of dodecyl benzene sulfonate or a linear alkyl sulfonate, and an acidulant selected from the group consisting of phosphoric acid, sulfuric acid, sulfuric acid, adipic acid, tartaric acid, succinic acid, acetic acid, fumaric acid, propionic acid, citric acid, malic acid, lactic acid, and mixtures thereof, wherein the volume ratio of carrier to antimicrobial is a minimum of about 256:1 and the compositional pH is from about 1.3 to 4.0.

4. A solid antimicrobial composition consisting essentially of a major portion of carrier, said carrier comprising a solidifying agent that is selected from the group consisting of an organic hardening agent, an inorganic hardening agent, and mixtures thereof; an antimicrobial consisting of about 0.01 wt-% 0.50 wt-%, based on the composition as a whole, of octanoic acid, an octanoic acid ester or salt thereof, and about 0.01 wt-% to 0.50 wt-%, based on the composition as a whole, of dodecyl benzene sulfonate or a linear alkyl sulfonate, and an acidulant selected from the group consisting of phosphoric acid, sulfuric acid, sulfamic acid, adipic acid, tartaric acid, succinic acid, acetic acid, fumaric acid, propionic acid, citric acid, malic acid, lactic acid, and mixtures thereof.

5. A liquid concentrate antimicrobial composition comprising:
   (a) an antimicrobial agent consisting of about 0.5–45 wt-% octanoic acid, an octanoic acid ester or salt thereof, and about 0.5–45 wt-% of dodecyl benzene sulfonic acid;
   (b) from about 0.1 to 90 wt-% hexylene glycol;
   (c) from about 0.02 to 40 wt-% nonionic surfactant, said surfactant comprising from about 5 to 15 moles ethylene oxide and from about 10 to 30 moles propylene oxide; and
   (d) a balance of water.

6. The composition of claim 3 wherein said carrier is present in a concentration ranging from about 54 wt-% to 98 wt-%.

7. The composition of claim 3 wherein said carrier comprises water.

8. The composition of claim 4, wherein said organic solidifying agent is selected from the group consisting of urea, alkyl and dialkyl phenol ethoxylates, linear alkyl alcohol ethoxylates, polyalkoxide block polymers of ethanolamines, polyethylene glycol, polyoxyethylenepolyoxypropylene polymers or mixtures thereof.

9. The composition of claim 4 wherein said solidifying agent is present in a concentration ranging from about 40 wt-% to 99 wt-%.

* * * * *